United States Patent
Linder et al.

(10) Patent No.: US 8,792,992 B2
(45) Date of Patent: Jul. 29, 2014

(54) LOW-POWER SYSTEM AND METHODS FOR NEUROMODULATION

(75) Inventors: William J. Linder, Golden Valley, MN (US); Keith R. Maile, New Brighton, MN (US); Ramprasad Vijayagopal, Shoreview, MN (US); Ron A. Balczewski, Bloomington, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 128 days.

(21) Appl. No.: 13/274,448

(22) Filed: Oct. 17, 2011

(65) Prior Publication Data

US 2012/0116482 A1 May 10, 2012

Related U.S. Application Data

(60) Provisional application No. 61/412,114, filed on Nov. 10, 2010.

(51) Int. Cl.
*A61N 1/00* (2006.01)

(52) U.S. Cl.
USPC ............ 607/62; 607/2; 607/7; 607/8; 607/28; 607/63; 607/64

(58) Field of Classification Search
USPC ................... 607/2, 7, 8, 28, 62–64
See application file for complete search history.

(56) References Cited

U.S. PATENT DOCUMENTS

| 4,354,498 | A | * | 10/1982 | Weigert et al. | 607/64 |
|---|---|---|---|---|---|
| 4,363,324 | A | * | 12/1982 | Kusserow | 607/64 |
| 5,540,724 | A | * | 7/1996 | Cox | 607/8 |
| 5,690,683 | A | | 11/1997 | Haefner et al. | |
| 5,836,983 | A | | 11/1998 | Weijand et al. | |
| 6,317,628 | B1 | | 11/2001 | Linder et al. | |
| 7,216,000 | B2 | | 5/2007 | Sieracki et al. | |
| 7,389,147 | B2 | | 6/2008 | Wahlstrand et al. | |
| 7,493,161 | B2 | | 2/2009 | Libbus et al. | |
| 7,881,782 | B2 | | 2/2011 | Libbus et al. | |
| 8,036,739 | B2 | | 10/2011 | Ternes | |
| 2002/0068957 | A1 | * | 6/2002 | Wolfe et al. | 607/2 |
| 2005/0283197 | A1 | | 12/2005 | Daum et al. | |
| 2006/0095080 | A1 | | 5/2006 | Libbus et al. | |
| 2006/0271118 | A1 | | 11/2006 | Libbus et al. | |

(Continued)

OTHER PUBLICATIONS

Foutz, T. J., et al., "Energy Efficient Neural Stimulation: Coupling Circuit Design and Membrane Biophysics", PLOS ONE, www.plosone.org; vol. 7, Issue 12, e51901, (Dec. 2012), 1-8.

(Continued)

*Primary Examiner* — Michael Kahelin
*Assistant Examiner* — Mallika D Fairchild
(74) *Attorney, Agent, or Firm* — Schwegman, Lundberg & Woessner, P.A.

(57) ABSTRACT

An apparatus comprises an electrostimulation energy storage capacitor, a circuit path communicatively coupled to the electrostimulation energy storage capacitor and configured to provide quasi-constant current neural stimulation through a load from the electrostimulation energy storage capacitor, a current measuring circuit communicatively coupled to the circuit path and configured to obtain a measure of quasi-constant current delivered to the load, and a control circuit communicatively coupled to the current measuring circuit, wherein the control circuit is configured to initiate adjustment of the voltage level of the storage capacitor for a subsequent delivery of quasi-constant current according to a comparison of the measured load current to a specified load current value.

18 Claims, 7 Drawing Sheets

(56) References Cited

U.S. PATENT DOCUMENTS

| | | |
|---|---|---|
| 2009/0156957 A1 | 6/2009 | Linder et al. |
| 2009/0157132 A1 | 6/2009 | Linder et al. |
| 2010/0010553 A1 | 1/2010 | Libbus et al. |
| 2010/0298897 A1 | 11/2010 | Chavan et al. |
| 2011/0224747 A1 | 9/2011 | Maile et al. |
| 2013/0073008 A1 | 3/2013 | Ternes et al. |

OTHER PUBLICATIONS

US 7,684,855, 03/2010, Giftakis et al. (withdrawn)

* cited by examiner

LOW-POWER SYSTEM AND METHODS FOR NEUROMODULATION

CROSS-REFERENCE TO RELATED APPLICATIONS

This application claims the benefit of U.S. Provisional Application No. 61/412,114, filed on Nov. 10, 2010, under 35 U.S.C. §119(e), which is incorporated herein by reference in its entirety.

BACKGROUND

Implantable medical devices (IMDs) include, among other things, cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural or neuro-stimulation capability. CFM devices typically use pacing output circuits dedicated to provide output voltage pulses, while neural stimulation devices typically use output circuits dedicated to provide constant current.

OVERVIEW

This document discusses examples of techniques for generating and delivering neural stimulation therapy. In particular, it relates to devices and methods to delivery of quasi-constant current therapy.

An apparatus example includes an electrostimulation energy storage capacitor, a circuit path communicatively coupled to the electrostimulation energy storage capacitor that provides quasi-constant current neural stimulation through a load from the electrostimulation energy storage capacitor, a current measuring circuit communicatively coupled to the circuit path that obtains a measure of quasi-constant current delivered to the load, and a control circuit communicatively coupled to the current measuring circuit. The control circuit initiates adjustment of the voltage level of the storage capacitor for a subsequent delivery of quasi-constant current according to a comparison of the measured load current to a specified load current value.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A medical device may include one or more of the features, structures, methods, or combinations thereof described herein. For example, a cardiac stimulator may be implemented to include one or more of the advantageous features or processes described below. It is intended that such a monitor, stimulator, or other implantable, partially implantable, ambulatory, or wearable device need not include all of the features described herein, but may be implemented to include selected features that provide for unique structures or functionality. Such a device may be implemented to provide a variety of therapeutic or diagnostic functions.

Figure 1:
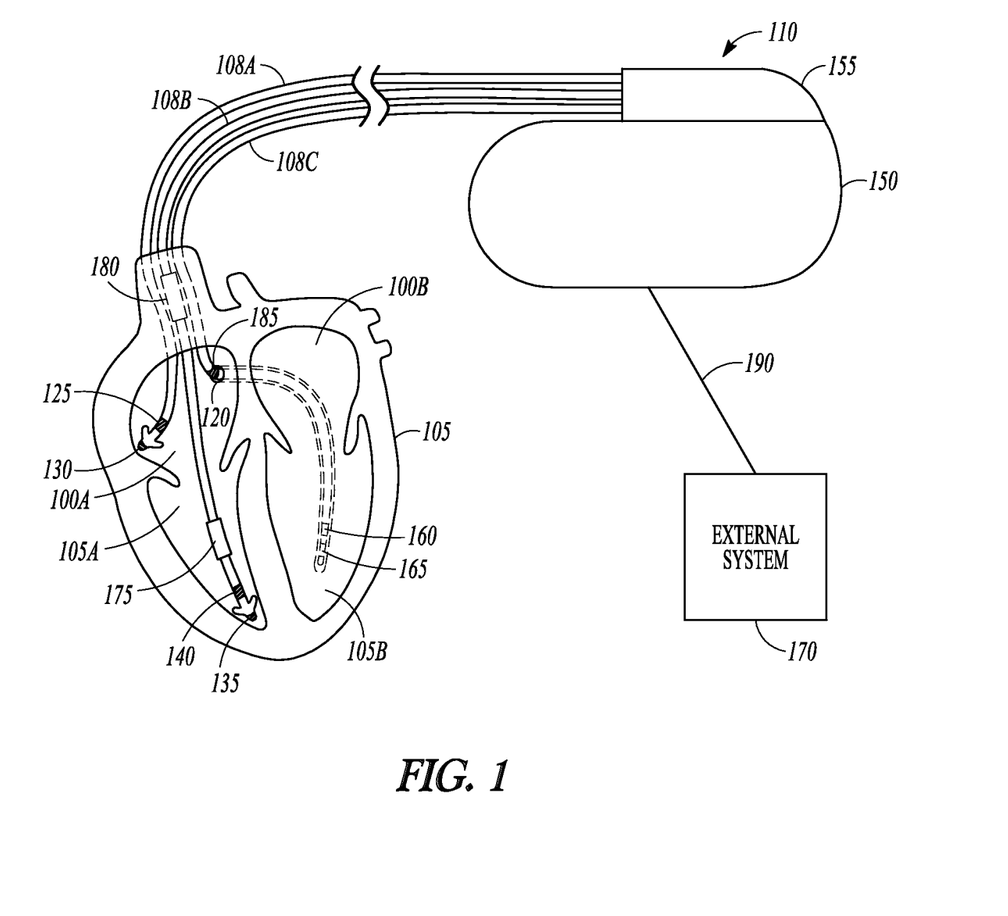
FIG. 1 is an illustration of an example of portions of a system that includes an implantable medical device.

This document discusses devices and methods for generating and delivering neural stimulation therapy. An ambulatory medical device includes medical devices that can be worn, implanted, or partially implanted. FIG. 1 is an illustration of portions of a system 100 that uses an implantable medical device (IMD) 110. Examples of IMD 110 include, without limitation, a pacer, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 is coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 may include a third cardiac lead 108C attached to the IMD 110 through the header 155. The third cardiac lead 108C includes electrodes 160 and 165 placed in a coronary vein lying epicardially on the left ventricle (LV) 105B via the coronary vein. The third cardiac lead 108C may include a ring electrode 185 positioned near the coronary sinus (CS) 182.

Lead 108B may include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown the illustration, the present methods and systems will work in a variety of configurations and with a variety of electrodes. Other forms of electrodes include meshes and patches which may be applied to portions of heart 105 or which may be implanted in other areas of the body to help "steer" electrical currents produced by IMD 110. Electrode configurations can include a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

An IMD that delivers neural stimulation therapy can include leads and electrodes designed for placement to provide therapy to specific areas of the nervous system, including the sympathetic nervous system and the parasympathetic nervous system. The sympathetic nervous system is associated with increased blood flow, heart rate, and increased skeletal muscle blood flow. The parasympathetic nervous system is associated with decreased blood pressure, heart rate, and increased digestion.

Stimulating the sympathetic and parasympathetic nervous systems can affect other areas besides heart rate and blood pressure. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, and increases digestion in the small intention, increases urine secretion, and contracts the wall and relaxes the sphincter of the bladder. The functions associated with the sympathetic and parasympathetic nervous systems are many and can be complexly integrated with each other.

Baroreflex is a reflex triggered by stimulation of a baroreceptor. A baroreceptor includes any sensor of pressure changes, such as sensory nerve endings in the wall of the auricles of the heart, vena cava, aortic arch and carotid sinus, that is sensitive to stretching of the wall resulting from increased pressure from within, and that functions as the receptor of the central reflex mechanism that tends to reduce that pressure. Clusters of nerve cells can be referred to as autonomic ganglia. These nerve cells can also be electrically stimulated to induce a baroreflex, which inhibits the sympathetic nerve activity and stimulates parasympathetic nerve activity. Autonomic ganglia thus forms part of a baroreflex pathway. Afferent nerve trunks, such as the vagus, aortic and carotid nerves, leading from the sensory nerve endings also form part of a baroreflex pathway. Stimulating a baroreflex pathway and/or baroreceptors inhibits sympathetic nerve activity (stimulates the parasympathetic nervous system) and reduces systemic arterial pressure by decreasing peripheral vascular resistance and cardiac contractility. Baroreceptors are naturally stimulated by internal pressure and the stretching of vessel wall (e.g. arterial wall).

In some examples, a neural stimulation device may locally stimulate specific nerve endings in arterial walls rather than stimulate afferent nerve trunks in an effort to stimulate a desired response (e.g. reduced hypertension) while reducing the undesired effects of indiscriminate stimulation of the nervous system. In certain examples, baroreceptor sites in the pulmonary artery are stimulated. In some examples, a neural stimulation device stimulates baroreceptor sites or nerve endings in the aorta and the chambers of the heart, and/or an afferent nerve trunk, such as the vagus, carotid and aortic nerves. In some examples, neural stimulation devices stimulate afferent nerve trunks using a cuff electrode, and some embodiments stimulate afferent nerve trunks using an intravascular lead positioned in a blood vessel proximate to the nerve, such that the electrical stimulation passes through the vessel wall to stimulate the afferent nerve trunk.

Figure 2:
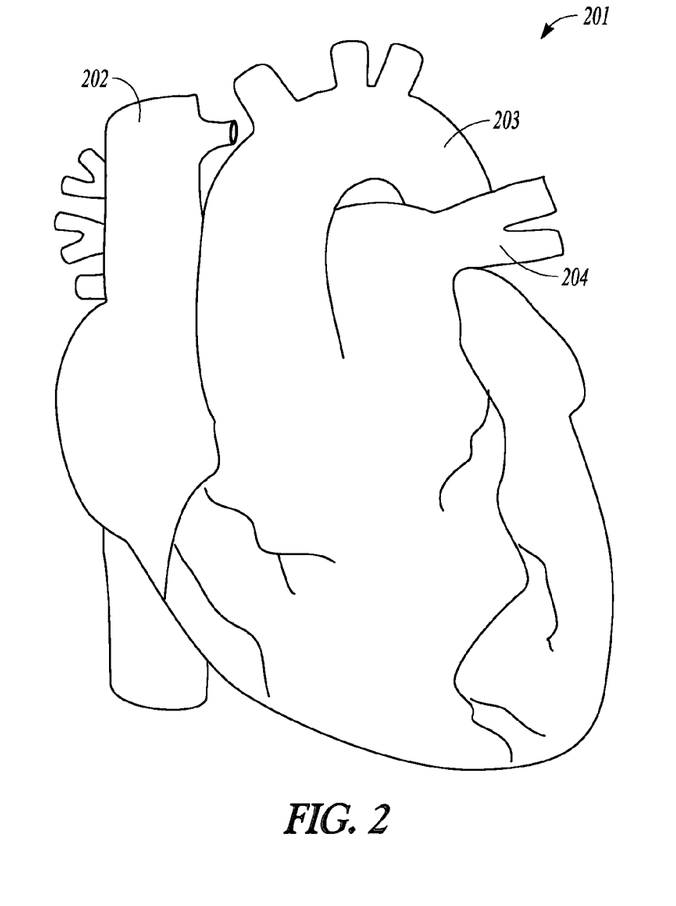
FIG. 2 is an illustration of a heart including the superior vena cava, the aortic arch, and the pulmonary artery.

FIG. 2 illustrates a heart. The heart 201 includes a superior vena cava 202, an aortic arch 203, and a pulmonary artery 204. The pulmonary artery 204 includes baroreceptors. A lead is capable of being intravascularly inserted through a peripheral vein and through the tricuspid valve into the right ventricle of the heart (not expressly shown in the figure) similar to a cardiac pacemaker lead described above, and continue from the right ventricle through the pulmonary valve into the pulmonary artery. A portion of the pulmonary artery and aorta are proximate to each other. Various embodiments stimulate baroreceptors in the aorta using a lead intravascularly positioned in the pulmonary artery. Thus, according to various aspects of the present subject matter, the baroreflex is stimulated in or around the pulmonary artery by at least one electrode intravascularly inserted into the pulmonary artery.

Alternatively, a wireless stimulating device, with or without pressure sensing capability, may be positioned via catheter into the pulmonary artery. Control of stimulation and/or energy for stimulation may be supplied by another implantable or external device via ultrasonic, electromagnetic or a combination thereof. Aspects of the present subject matter provide a relatively noninvasive surgical technique to implant a baroreflex stimulator intravascularly into the pulmonary artery.

Figure 3:
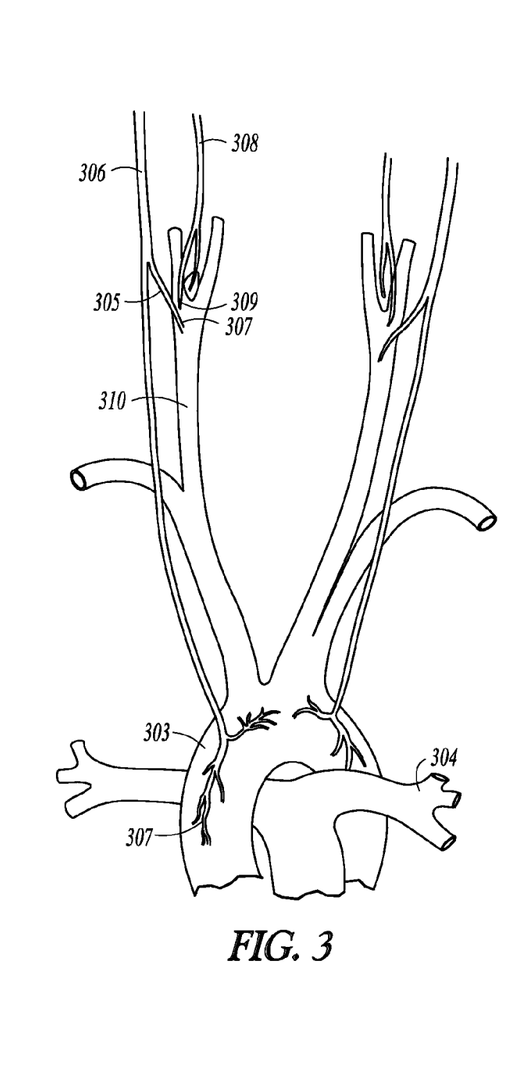
FIG. 3 illustrates baroreceptors in the area of the carotid sinus, aortic arch, and pulmonary artery.

FIG. 3 illustrates baroreceptors in the area of the carotid sinus 305, aortic arch 303, and pulmonary artery 304. The aortic arch 303 and pulmonary artery 304 were previously illustrated with respect to the heart in FIG. 2. As illustrated in FIG. 3, the vagus nerve 306 extends and provides sensory nerve endings 307 that function as baroreceptors in the aortic arch 303, in the carotid sinus 305 and in the common carotid artery 310. The glossopharyngeal nerve 308 provides nerve endings 309 that function as baroreceptors in the carotid sinus 305. These nerve endings 307 and 309, for example, are sensitive to stretching of the wall resulting from increased pressure from within. Activation of these nerve endings reduces pressure. Although not illustrated in the figures, the atrial and ventricular chambers of the heart also include baroreceptors. Cuffs can be placed around afferent nerve trunks, such as the vagal nerve, leading from baroreceptors to vasomotor centers to stimulate the baroreflex. The cuffs can include electrodes for delivering neural stimulation energy. According to various embodiments of the present subject matter, afferent nerve trunks can be stimulated using a cuff or an intravascularly-fed lead positioned in a blood vessel proximate to the afferent nerves.

Pacing therapy includes cardiac contractile electrostimulation. The stimulation is provided as output voltage pulses to cause depolarization of cardiac cells and contraction of the myocardium. Pacing stimulation can be delivered to the heart as pulses of quasi-constant voltage output.

Figure 4:
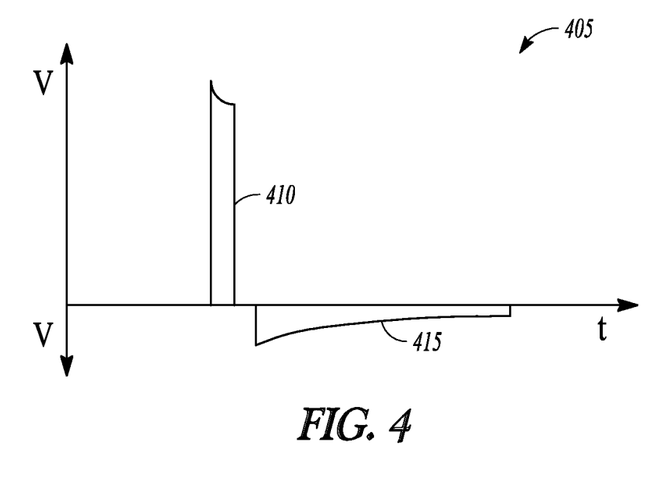
FIG. 4 shows an example of a pacing stimulation pulse.

FIG. 4 shows an example of a pacing stimulation pulse 405. The pacing stimulation pulse 405 can be referred to as a quasi-constant voltage, or a virtually constant voltage, because there can be some droop of the amplitude of the pulse. This droop is the result of the RC time constant of the output circuit. In some examples, the pacing stimulation pulse can involve two portions.

The first portion 410 is to initiate a depolarization of myocardial cells. In some examples, the amplitude of the first portion 410 is programmable. The second portion 415 includes a charge-restoring stimulus to dissipate after-potentials resulting from delivery of the first portion 410 of the pacing stimulation. This can reduce the chance of a DC charge accumulating at the electrode/tissue interface. Without the charge-restoring stimulus, the accumulation of charge can reduce the effectiveness of the first portion of the pacing stimulation.

Figure 5:
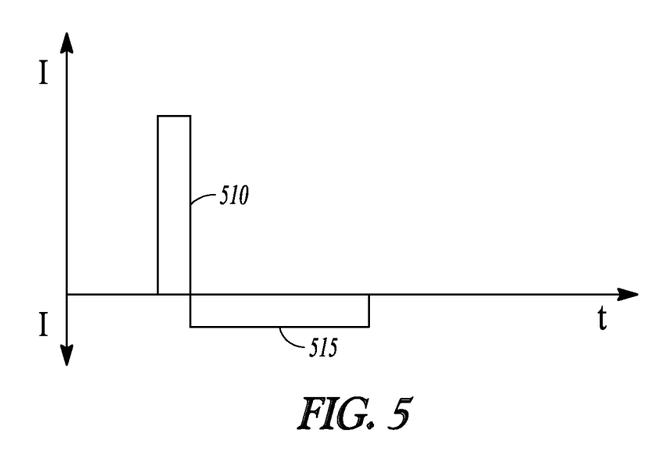
FIG. 5 shows an example of a neural stimulation pulse.

Neural stimulation involves providing energy of constant current to nerves and is not intended to be contractile. FIG. 5 shows an example of a neural stimulation pulse 505. In some examples, the neural stimulation pulse 505 can involve two portions. The first portion 510 and the second portion 515 are current pulses of constant current amplitude. The second portion 515 restores the balance of charge at the electrode/tissue interface. In some examples, the amplitudes of one or both of the first and second portions 510 are programmable. Nerves can adapt to the stimulation, which can result in effectiveness of neural stimulation therapy diminishing over time. The neural stimulation can be modulated to mimic the effects of naturally occurring stimulation and to prevent adaptation of the nerves to the artificial stimulation. For example, the amplitude, frequency, wave morphology, burst frequency and/or duration can be adjusted to abate adaptation.

Figure 6:
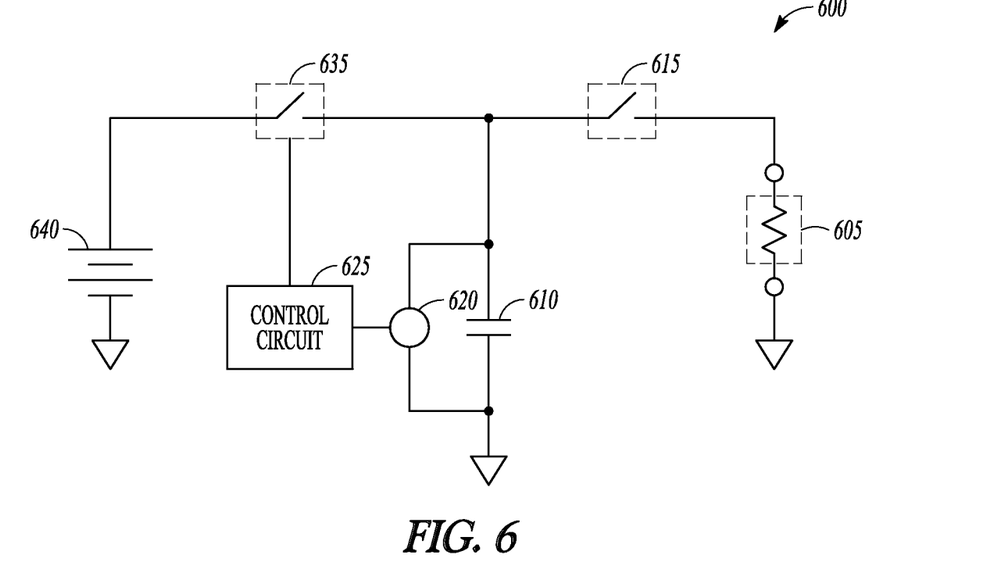
FIG. 6 shows a block diagram of portions of an example of a device therapy circuit that provides quasi-constant current neural stimulation therapy through a load.

FIG. 6 is a block diagram of portions of an example of a device therapy circuit 600 that provides quasi-constant current neural stimulation therapy through a load 605. Examples of the load 605 include, among other things, specific areas of the myocardium and specific areas of the nervous system of a patient or subject. The therapy circuit 600 includes an electrostimulation energy storage capacitor 610 and a circuit path communicatively coupled to the electrostimulation energy storage capacitor 610. To provide energy for the therapy, an energy supply 640 (e.g., a battery) can be used to pre-charge the electrostimulation energy storage capacitor 610.

The therapy circuit 600 includes a current measuring circuit 620 communicatively coupled to the therapy circuit 600 that obtains a measure of quasi-constant current delivered to the load. The therapy circuit 600 also includes a control circuit 625 communicatively coupled to the current measuring circuit 620. The communicative coupling allows the control circuit 625 to communicate signals with the current measuring circuit even though there may be intervening circuitry between the control circuit 625 and the current measuring circuit 620.

The control circuit 625 provides the timing of the therapy. The control circuit 625 may include a processor such as a microprocessor, a digital signal processor, application specific integrated circuit (ASIC), microprocessor, or other type of processor, interpreting or executing instructions in software or firmware. The control circuit 625 can include other circuits or sub-circuits to perform the functions described. These circuits may include software, hardware (e.g., logic circuits), firmware or any combination thereof. Multiple functions can be performed in one or more of the circuits as desired. In some examples, the control circuit 625 can include a state machine implemented in hardware (e.g., logic circuits) to transition the control circuit 625 to different device states that correspond to device functions.

The control circuit 625 initiates the quasi-constant current stimulation by pre-charging the electrostimulation energy storage capacitor 610 using the supply switch 635 and electrically connecting the capacitor 610 to the load 605 via electrodes. Thus, the circuit path provides quasi-constant current neural stimulation through a load from the electrostimulation energy storage capacitor 610. The circuit path begins at the storage capacitor and continues through the load 605. In some examples, the circuit path includes a therapy switch circuit 615. The therapy delivered is quasi-constant current because there can be some droop of the amplitude of the delivered current stimulation pulse.

The control circuit 625 initiates adjustment of the voltage level of the storage capacitor 610 for a subsequent delivery of quasi-constant current according to a comparison of the measured load current to a specified load current value.

The therapy circuit 600 uses a capacitor to store energy for the quasi-constant current neural stimulation therapy. Ideally, inductors would be used to store the energy, but losses associated with inductors make this approach less feasible.

In some examples, the therapy circuit 600 is included in a battery powered device (e.g., an implantable medical device or IMD). Because a capacitor is used for energy storage, there is a need to optimize the amount of energy used to supply the current to the load. To preserve battery energy, the energy stored on the storage capacitor 610 should be reduced to a minimum required to provide the current stimulation to the load and to cover any amount of overhead needed by circuits used to deliver the current stimulation. This required energy varies with the impedance of the load. As the load increases, the voltage of the load increases to maintain the constant current therapy. This increases the required compliance voltage(s). Similarly, as the load decreases, the voltage of the load decreases. The required compliance voltage can be decreased to reduce the energy required to deliver the therapy. It is desired to maintain a compliance voltage that is sufficient for the circuits to work but does not waste current. As an illustrative example, the compliance voltage may be 200 millivolts (mV) above the voltage required for the load.

In some examples, the control circuit 625 recurrently initiates obtaining a measure of the delivered quasi-constant load current and adjusting the voltage level of the storage capacitor to minimize a difference between the measured quasi-constant current and the specified target load current. This allows the control circuit to tune or "dial in" the appropriate voltage level on the storage capacitor to provide the specified load current target as the impedance of the load changes. In some examples, the specified target load current is a programmable therapy parameter. The electrical impedance of the load may vary from patient to patient, may vary from therapy to therapy for the same patient, and may vary during the same delivery of therapy. Thus, it is desirable for the therapy circuit 600 to maintain the target load current over a range of load impedances.

Figure 7:
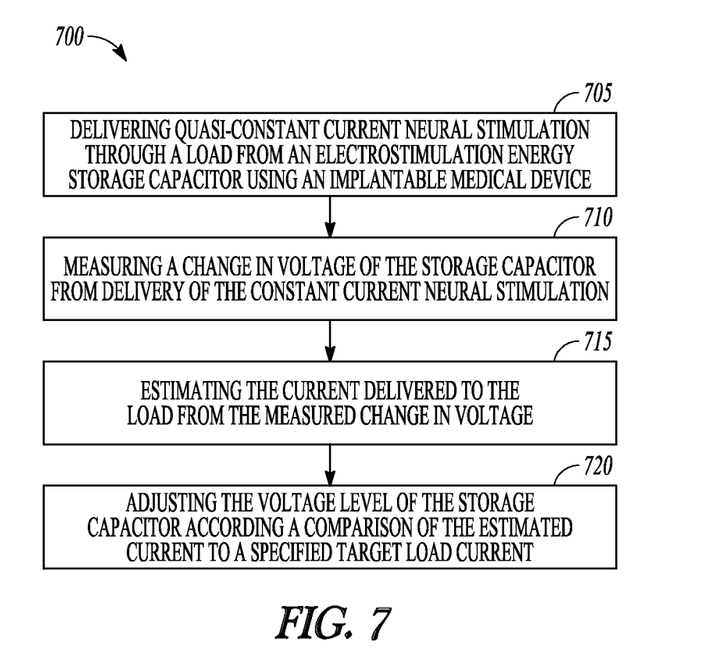
FIG. 7 shows a flow diagram of an example of a method to optimize energy used to deliver quasi-constant current stimulation therapy to a load.

FIG. 7 shows a flow diagram of an example of a method 700 to optimize energy used to deliver quasi-constant current stimulation therapy to a load. At block 705, quasi-constant current neural stimulation is delivered through a load from an electrostimulation energy storage capacitor using an IMD, such as by the therapy circuit 600 in FIG. 6 for example.

Figure 8:
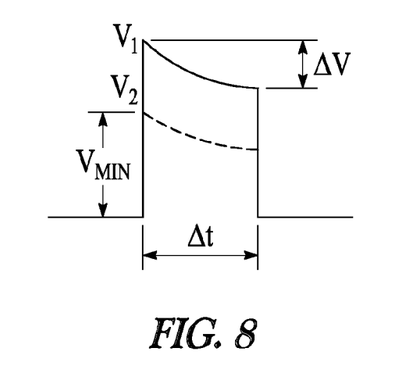
FIG. 8 is an example of a capacitor discharge curve.

At block 710, a change in voltage of the storage capacitor from delivery of the constant current neural stimulation is measured. As current is drawn from the storage capacitor, there is some droop in the voltage on the storage capacitor. This is shown in FIG. 8 where the droop is denoted as $\Delta V$.

At block 715, the current delivered to the load is estimated from the measured change in voltage. In some examples, the current is estimated using the equation for current $I=C\cdot\Delta V/\Delta t$, where I is the current delivered, C is the capacitance of the storage capacitor 610, $\Delta V$ is the measured droop of the voltage of the storage capacitor, and $\Delta t$ is the time over which the voltage droop occurred. In some examples, the $\Delta t$ is the pulse width or pulse duration of the constant current therapy.

At block 720, the voltage level of the storage capacitor is adjusted according a comparison of the estimated load current to a specified target load current. The voltage on the storage capacitor at the end of the current therapy pulse needs to be at least the minimum voltage Vmin to maintain compliance of the circuitry. An example of this is shown in the capacitor discharge curve of FIG. 8. If the voltage on the storage capacitor starts at voltage V1, the voltage on the storage capacitor will still be greater than the compliance voltage after the voltage droop occurs. If the voltage on the storage capacitor starts at voltage V2, the voltage on the storage capacitor will be less than the compliance voltage after the voltage droop occurs. This may result in the circuitry that delivers the constant current therapy not working properly. In some examples, the voltage level of the storage capacitor is changed to the minimum level required to source the specified current and maintain the compliance voltage (e.g., $\Delta V=I\cdot\Delta t/C$). In some examples, the voltage level of the storage capacitor is incremented or decremented by a specified voltage step. In this way, the optimum voltage for the storage capacitor can be tuned to provide the target load current.

Figure 9:
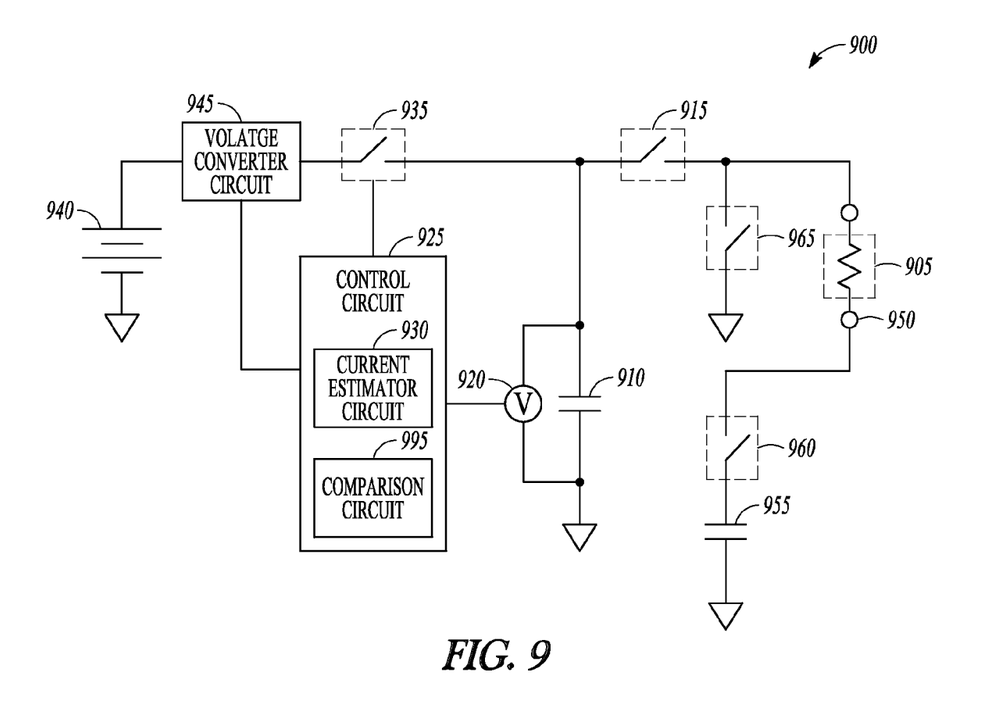
FIG. 9 is a block diagram of portions of another example of a device therapy circuit that provides quasi-constant current neural stimulation therapy through a load.

FIG. 9 is a block diagram of portions of another example of a device therapy circuit 900 that provides quasi-constant current neural stimulation therapy through a load 905. The therapy circuit 900 again includes an electrostimulation energy storage capacitor 910 and a control circuit 925.

The current measurement circuit includes a voltage measurement circuit 920 communicatively coupled to the storage capacitor 910 and a current estimator circuit 930 included in the control circuit 925. The voltage measurement circuit 920 measures a change in voltage of the storage capacitor resulting from delivery of the quasi-constant current neural stimulation. The current estimator circuit 930 estimates the quasi-constant current delivered to the load from the measured change in voltage of the storage capacitor, such as by the method in FIG. 7 for example.

In some examples, the control circuit 925 is configured to initiate an increase in the voltage level of the storage capacitor 910 to a minimum voltage level sufficient to operate the current measurement circuit and to provide the specified load current value. In some examples, the control circuit 925 is configured to initiate a reduction in the voltage level of the storage capacitor to a minimum voltage level sufficient to provide the specified load current value.

According to some examples, the circuit 900 includes a voltage converter circuit 945 (e.g., a DC-DC voltage converter) to change a voltage provided to the storage capacitor 910 via the supply switch 935. The voltage converter circuit 945 may include a programmable voltage reference circuit to provide a changeable reference voltage value. The voltage converter circuit 945 sets the voltage level of the storage capacitor 910 according to the reference voltage value. If the voltage (or a measured fraction of the voltage) of the storage capacitor 910 is less than the programmed voltage reference, the voltage converter circuit 945 increases the voltage on the storage capacitor 910. In some examples, the control circuit 925 initiates a change in the voltage of the storage capacitor 910 by changing the reference voltage value.

In some examples, the control circuit 925 includes a comparison circuit 995 to compare the estimated load current to the specified load current. The control circuit 925 recurrently initiates a comparison of the estimated load current to the specified load current value, recurrently increases the voltage of the storage capacitor by a specified voltage change when the estimated load current is less than the specified load current value, and recurrently decreases the voltage of the storage capacitor 910 by the specified voltage change when the estimated load current is greater than the specified load current value.

According to some examples, the therapy circuit 900 includes a recharge circuit communicatively coupled to a port 950 configured for electrical connection to the load 905. The recharge circuit may include a recharge capacitor 955. In some examples, the recharge circuit includes a recharge switch 960 and a return switch 965. The control circuit 925 can initiate a delivery of biphasic electrical neural therapy to the load 905. The biphasic therapy includes quasi-constant current neural stimulation during a first phase of the biphasic electrical neural therapy and includes delivery of a charge-restoring pulse in a second phase of energy delivery.

Figure 10:
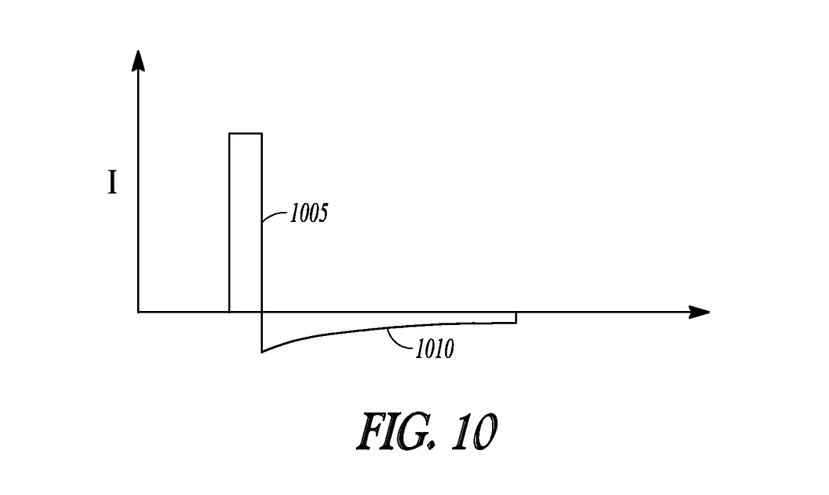
FIG. 10 shows an example of a hybrid current/charge-restoring therapy pulse.

FIG. 10 shows an example of such a hybrid current/charge-restoring therapy biphasic pulse. Quasi-constant current is delivered during the first phase 1005 of the biphasic electrical neural therapy. The quasi-constant current neural stimulation is delivered through the load 905 using energy stored on the storage capacitor 910. The recharge capacitor 955 stores the electrical energy from the quasi-constant current neural stimulation during the first phase. A charge-restoring pulse is delivered during the second phase 1010 of the biphasic electrical neural therapy. To generate the charge-restoring pulse, the recharge capacitor 955 discharges its stored electrical energy to the load 905. In some examples, the return switch 965 is open during the first phase and is closed during the second phase. In some examples, the control circuit 925 measures the change in voltage of the storage capacitor 910 during the first phase of the biphasic electrical neural therapy.

Note that, in comparison to the all current waveform of FIG. 5, energy for the delivery of the biphasic neural therapy is reduced by fifty percent. Thus, charge balance is maintained at the lead-tissue interface for half the energy cost of an all-current waveform. In the example shown, closing or otherwise activating switches 960 and 965 causes the recharge circuit to deliver a recharge-phase of the pulse having a polarity opposite to the polarity of the quasi-constant current neural stimulation. The second recharge-phase pulse restores charge balance at the load-tissue interface.

Figure 11:
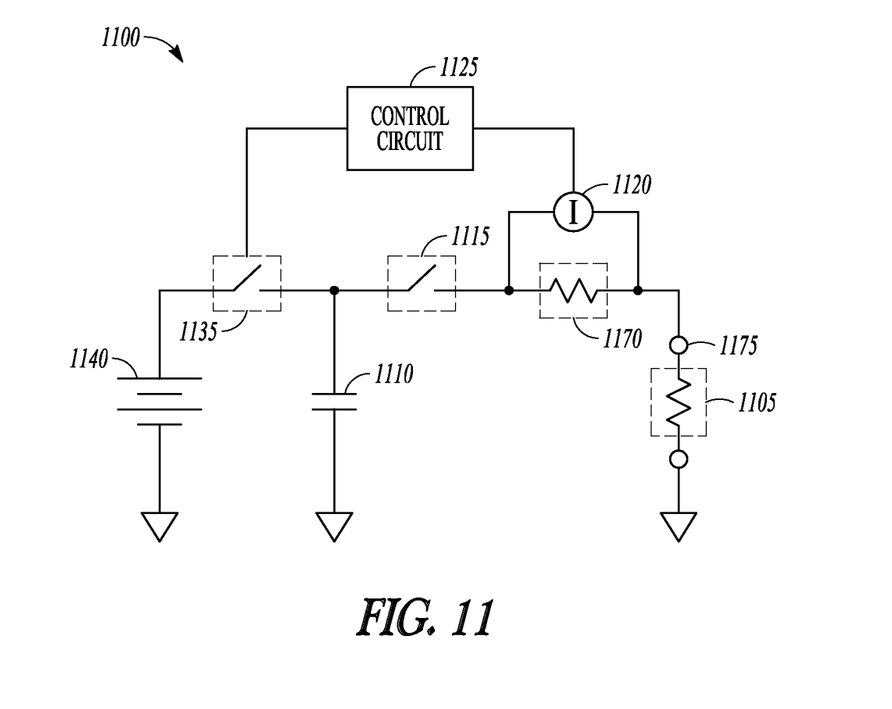
FIG. 11 is a block diagram of portions of another example of a device therapy circuit that provides quasi-constant current neural stimulation therapy through a load.

FIG. 11 is a block diagram of portions of another example of a device therapy circuit 1100 that provides quasi-constant current neural stimulation therapy through a load 1105. The therapy circuit 1100 again includes an electrostimulation energy storage capacitor 1110 and a control circuit 1125. The control circuit 1125 initiates the quasi-constant current stimulation by pre-charging the electrostimulation energy storage capacitor 1110 using the supply switch 1135 and electrically connecting the capacitor 1110 to the load 1105 via electrodes.

The circuit path includes a sense resistor 1170 arranged in series with a port 1175 configured for electrical connection to the load 1105. The current monitoring circuit 1120 is communicatively coupled to the sense resistor 1170. The current monitoring circuit 1120 measures a voltage across the sense resistor 1170 and obtains the measure of quasi-constant current delivered to the load using the measured voltage. The control circuit 1125 initiates adjustment of the voltage level of the storage capacitor 1110 for a subsequent delivery of quasi-constant current according to a comparison of the measured load current to a specified target load current value. In some examples, the control circuit 1125 initiates a reduction in the voltage level of the storage capacitor to a minimum voltage level sufficient to operate the current monitoring circuit 1120 and sense resistor 1170, and to provide the specified load current value.

Figure 12:
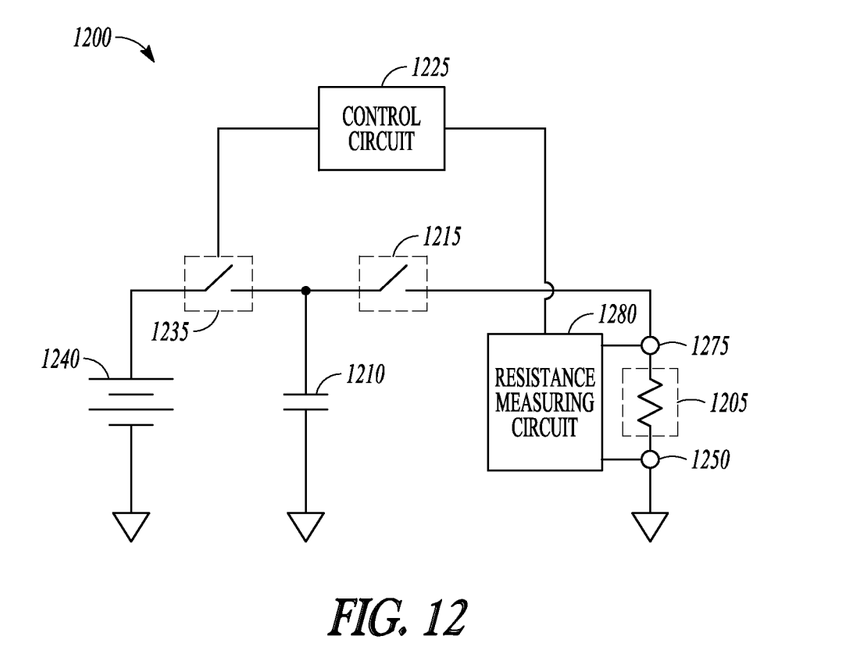
FIG. 12 is a block diagram of portions of another example of a device therapy circuit that provides quasi-constant current neural stimulation therapy through a load.

FIG. 12 is a block diagram of portions of another example of a device therapy circuit 1200 that provides quasi-constant current neural stimulation therapy through a load 1205. The therapy circuit 1200 again includes an electrostimulation energy storage capacitor 1210 and a control circuit 1225. The control circuit 1225 initiates the quasi-constant current stimulation from energy stored on the electrostimulation energy storage capacitor 1210.

The therapy circuit 1200 includes a resistance measuring circuit 1280 communicatively coupled to the circuit path to obtain a measure of resistance of the load 1205. The control circuit 1225 is configured to initiate adjustment of the voltage level of the storage capacitor 1210 for a delivery of quasi-constant current according to the measure of resistance and the target load current. In some examples, the resistance can be measured by applying a specified non-stimulating excitation current pulse across the load, such as between ports 1275 and 1250. The excitation current is non-stimulating because it has an amplitude lower than the minimum amplitude for pacing stimulation, i.e., it has a low enough amplitude that it does not trigger a heart depolarization or stimulate a nerve. The resulting voltage between the ports is then measured. The measured voltage is divided by the excitation current to obtain the resistance (e.g., $I_{STIM} = V_{STIM}/R_{LOAD}$). The control circuit 1225 sets the voltage of the storage capacitor 1210 to the voltage necessary to provide the target load current. In some examples, the voltage includes sufficient voltage to provide compliance for any circuits in the circuit path.

Examples of systems and methods of painless measurement of defibrillation lead impedance are found in Linder et al., U.S. Pat. No. 6,317,628, "Cardiac Rhythm Management System with Painless Defibrillation Lead Impedance Measurement," filed Jan. 25, 1999, which is incorporated herein in its entirety.

Figure 13:
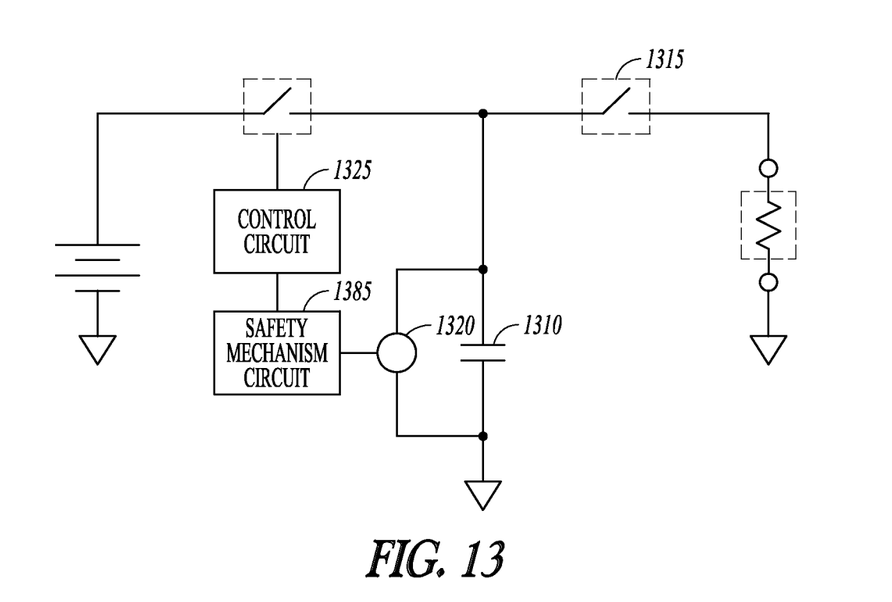
FIG. 13 is a block diagram of portions of the example device therapy circuit of FIG. 6 and including a safety mechanism circuit.

In some examples, a safety mechanism circuit is used to guard against excessive energy (e.g., runaway current) being delivered to the patient or subject. FIG. 13 is a block diagram of portions of the example therapy circuit of FIG. 6 with a safety mechanism circuit 1385. The safety mechanism circuit 1385 is communicatively coupled to the current measuring circuit 1320 and the control circuit 1325. The safety mechanism circuit 1385 monitors delivery of electrical energy during the quasi-constant current stimulation. The control circuit 1325 ends the constant current stimulation when the safety mechanism circuit 1385 indicates that the electrical energy exceeds a specified energy level threshold.

In some examples, the safety mechanism circuit 1385 is communicatively coupled to the voltage measuring circuit 920 of FIG. 9. The safety mechanism circuit 1385 may determine that the electrical energy exceeds a specified energy level threshold if the change in voltage of the storage capacitor 1310 exceeds a threshold voltage change value. In certain examples, the safety mechanism circuit 1385 includes a comparator circuit to detect a change in voltage that exceeds the threshold value. In some examples, the safety mechanism circuit 1385 detects a rate of discharge of the electrical energy that exceeds a specified threshold discharge rate.

In some examples, the safety mechanism circuit 1385 is communicatively coupled to the sense resistor 1170 in FIG. 11 and monitors current through the sense resistor 1170. In certain examples, the security mechanism circuit 1385 includes an amplifier coupled to the sense resistor 1170. The output of the sense amplifier is coupled to a first input of a comparator circuit. The second input of the comparator is coupled to a voltage reference circuit. An over-current condition is detected when the voltage drop across the sense resistor exceeds the voltage value of the voltage reference. In some examples, the voltage reference is programmable.

When the safety mechanism circuit indicates that the electrical energy delivered exceeds a specified energy level threshold (e.g., an excessive voltage change at the capacitor or an over-current condition at the sense resistor or the load), the control circuit 1325 ends the quasi-constant current stimulation. In certain examples, the control circuit 1325 opens therapy switch 1315 to end the quasi-constant current stimulation by immediately truncating the current therapy pulse. In certain examples, the control circuit 1325 terminates charging of the storage capacitor 1310 (such as by deactivating a voltage converter circuit 945 of FIG. 9) to end the therapy.

Devices and methods are described herein to efficiently operate a quasi-constant current therapy delivery system. This improvement automatically finds the minimum overhead operating voltage required for the circuitry used to deliver the quasi-constant current stimulation. The use of a hybrid therapy pulse also reduces the energy used to maintain charge balance at the lead-tissue interface.

Additional Notes and Examples

Devices and methods for generating and delivering quasi-constant current neural stimulation therapy are described herein.

Example 1 includes subject matter (such as an implantable or ambulatory apparatus) comprising an electro stimulation energy storage capacitor, communicatively coupled to a circuit path to provide quasi-constant current neural stimulation through a load from the electrostimulation energy storage capacitor, a current measuring circuit communicatively coupled to the circuit path and configured to obtain a measure of quasi-constant current delivered to the load, and a control circuit communicatively coupled to the current measuring circuit, wherein the control circuit is configured to initiate adjustment of the voltage level of the storage capacitor for a subsequent delivery of quasi-constant current according to a comparison of the measured load current to a specified load current value.

In Example 2, the control circuit of Example 1 can optionally be configured to recurrently initiate obtaining a measure of the delivered quasi-constant load current and adjusting the voltage level of the storage capacitor to minimize a difference between the measured quasi-constant current and the specified target load current.

In Example 3, the subject matter of one or any combination of Examples 1-2 optionally includes a voltage measuring circuit communicatively coupled to the storage capacitor and configured to measure a change in voltage of the storage capacitor resulting from delivery of the quasi-constant current neural stimulation, and the control circuit optionally includes a current estimator circuit configured to estimate the quasi-constant current delivered to the load from the measured change in voltage of the storage capacitor.

In Example 4, the control circuit of one or any combination of Examples 1-3 can optionally be configured to initiate a delivery of biphasic electrical neural therapy to the load including delivery of quasi-constant current neural stimulation during a first phase of the biphasic electrical neural therapy, and the measuring a change in voltage of the storage capacitor can optionally include measuring the change in voltage during the first phase of the biphasic electrical neural therapy.

In Example 5, the subject matter of one or any combination of Examples 1-4 can optionally include a recharge circuit communicatively coupled to a port configured for electrical connection to the load, and the recharge circuit can include a recharge capacitor. The recharge capacitor can be configured to store electrical energy from the quasi-constant current neural stimulation during the first phase of the biphasic electrical neural therapy, and discharge the electrical energy to the load during a second phase of the biphasic electrical neural therapy.

In Example 6, the circuit path of one or any combination of Examples 1-5 can optionally include a sense resistor arranged in series with a port configured for electrical connection to the load. The current monitoring circuit can optionally be configured to measure a voltage across the sense resistor and obtain the measure of quasi-constant current delivered to the load using the measured voltage.

In Example 7, the subject matter of one or any combination of Examples 1-6 can optionally include a resistance measuring circuit communicatively coupled to the circuit path to obtain a measure of resistance of the load, and the control circuit can optionally be configured to initiate adjustment of the voltage level of the storage capacitor for a delivery of quasi-constant current according to the measure of resistance and the target load current.

In Example 8, the control circuit of one or any combination of Examples 1-7 can optionally be configured to initiate a reduction in the voltage level of the storage capacitor to a minimum voltage level sufficient to operate the current measurement circuit and to provide the specified load current value.

In Example 9, the subject matter of one or any combination of Examples 1-8 can optionally include a voltage reference circuit configured to provide a changeable reference voltage value, and a voltage converter circuit, communicatively coupled to the storage capacitor and the voltage reference circuit, configured to provide energy to the storage capacitor according to the reference voltage value. The control circuit can be optionally configured to initiate adjustment of the voltage level of the storage capacitor by changing the reference voltage value.

In Example 10, the subject matter of one or any combination of Examples 1-9 can optionally include a safety mechanism circuit communicatively coupled to the voltage measuring circuit and the control circuit. The safety mechanism circuit can optionally be configured to monitor delivery of electrical energy during the constant current stimulation, and the control circuit can optionally be configured to end the constant current stimulation when the safety mechanism circuit indicates that the electrical energy exceeds a specified energy level threshold.

Example 11 can include subject matter, or can optionally by combined with the subject matter of one or any combination of Examples 1-10 to include subject matter (such as a method, a means for performing acts, or a machine-readable medium including instructions that, when performed by the machine, cause the machine to perform acts), comprising delivering quasi-constant current neural stimulation through a load from an electrostimulation energy storage capacitor using an implantable or ambulatory medical device, obtaining, using the device, a measure of the quasi-constant current delivered to the load, and adjusting, using the device, the voltage level of the storage capacitor for a subsequent quasi-constant current neural stimulation according to a comparison of the measure of quasi-constant current to a specified target load current.

In Example 12, the subject matter of Example 11 can optionally include recurrently obtaining the measure of the delivered quasi-constant load current and adjusting the voltage level of the storage capacitor to minimize a difference between the measured quasi-constant current and the specified target load current.

In Example 13, the subject matter of one or any combination of Examples 11-12 can optionally include measuring a change in voltage of the storage capacitor from delivery of the quasi-constant current neural stimulation, and the obtaining a measure of current can optionally include estimating the quasi-constant current delivered to the load from the measured change in voltage and duration of quasi-constant neural stimulation.

In Example 14, the subject matter of one or any combination of Examples 11-13 can optionally include delivering biphasic electrical neural therapy to the load. The delivering quasi-constant current neural stimulation can optionally include delivering quasi-constant current neural stimulation during a first phase of the biphasic electrical neural therapy, and the measuring a change in voltage of the storage capacitor can optionally include measuring the change during the first phase of the biphasic electrical neural therapy.

In Example 15, the subject matter of one or any combination of Examples 1-14 can optionally include measuring voltage across a sense resistor in series with the load, and the obtaining a measure of current can optionally include measuring the quasi-constant current delivered to the load using the measured voltage.

In Example 16, the subject matter of one or any combination of Examples 1-15 can optionally include obtaining a measure of resistance of the load, and the adjusting the voltage level of the storage capacitor can optionally include adjusting the voltage level of the storage capacitor according to the determined resistance and the target load current.

In Example 17, the adjusting the voltage level of the storage capacitor of one or any combination of Examples 1-16 can optionally include reducing the voltage level of the storage capacitor to a minimum voltage level required to operate a current measuring circuit and to provide the specified target load current.

In Example 18, the delivering quasi-constant current neural stimulation to a load of one or any combination of Examples 11-17 can optionally include delivering quasi-constant current neural stimulation through the load in a first phase of energy delivery, and delivering a voltage pulse to the load in a second phase of energy delivery.

In Example 19, the subject matter of one or any combination of Examples 11-18 can optionally include charging a second capacitor using the constant current neural stimulation delivered through the load in the first phase, and the delivering a voltage pulse can optionally include delivering a voltage pulse to the load from the second capacitor in the second phase of energy delivery.

In Example 20, the subject matter of one or any combination of Examples 11-19 can optionally include monitoring electrical energy delivered to the load during the quasi-constant current stimulation and ending the quasi-constant current stimulation if at least one of the electrical energy exceeds a specified energy level threshold and a rate of discharge of the electrical energy exceeds a specified threshold discharge rate.

Example 21 includes subject matter (such as an implantable or ambulatory apparatus) comprising an electro stimulation energy storage capacitor, communicatively coupled to a circuit path to provide quasi-constant current neural stimulation through a load from the electrostimulation energy storage capacitor, a resistance measuring circuit communicatively coupled to the circuit path and configured to obtain a measure of quasi-constant current delivered to the load, and a control circuit communicatively coupled to the current measuring circuit, wherein the control circuit is configured to initiate adjustment of the voltage level of the storage capacitor for a subsequent delivery of quasi-constant current according to the measure of resistance and the target load current.

Example 22 can include, or can optionally be combined with any portion or combination of any portions of any one or more of Examples 1-21 to include, subject matter that can include means for performing any one or more of the functions of Examples 1-21, or a machine-readable medium including instructions that, when performed by a machine, cause the machine to perform any one or more of the functions of Examples 1-21.

These examples can be combined in any permutation or combination. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable or other ambulatory apparatus comprising:
   an electrostimulation energy storage capacitor, communicatively coupled to a circuit path to provide quasi-constant current neural stimulation through a load from the electrostimulation energy storage capacitor;

a current measuring circuit communicatively coupled to the circuit path and configured to obtain a measure of quasi-constant current delivered to the load;

a control circuit communicatively coupled to the current measuring circuit, wherein the control circuit is configured to initiate a delivery of biphasic electrical neural therapy to the load including delivery of quasi-constant current neural stimulation during a first phase of the biphasic electrical neural therapy and determine, according to the measure of quasi-constant current delivered to the load, a voltage level sufficient to source the measured quasi-constant current, and initiate adjustment of the voltage level of the storage capacitor to the determined voltage level for a subsequent delivery of quasi-constant current; and a recharge circuit communicatively coupled to a port configured for electrical connection to the load, wherein the recharge circuit includes a recharge capacitor, wherein the recharge capacitor is configured to:

store electrical energy from the quasi-constant current neural stimulation during the first phase of the biphasic electrical neural therapy; and discharge the electrical energy to the load during a second phase of the biphasic electrical neural therapy.

2. The apparatus of claim 1, wherein the control circuit is configured to recurrently initiate obtaining a measure of the delivered quasi-constant load current and adjusting the voltage level of the storage capacitor to minimize a difference between the measured quasi-constant current and the specified target load current.

3. The apparatus of claim 1, including:

a voltage measuring circuit communicatively coupled to the storage capacitor and configured to measure a change in voltage of the storage capacitor resulting from delivery of the quasi-constant current neural stimulation, and wherein the control circuit includes a current estimator circuit configured to estimate the quasi-constant current delivered to the load from the measured change in voltage of the storage capacitor.

4. The apparatus of claim 3, wherein measuring a change in voltage of the storage capacitor includes measuring the change in voltage during the first phase of the biphasic electrical neural therapy.

5. The apparatus of claim 1, wherein the circuit path includes a sense resistor arranged in series with a port configured for electrical connection to the load, and wherein the current monitoring circuit is configured to measure a voltage across the sense resistor and obtain the measure of quasi-constant current delivered to the load using the measured voltage.

6. The apparatus of claim 1, including:

a resistance measuring circuit communicatively coupled to the circuit path to obtain a measure of resistance of the load, and wherein the control circuit is configured to initiate adjustment of the voltage level of the storage capacitor for a delivery of quasi-constant current according to the measure of resistance and the target load current.

7. The apparatus of claim 1, wherein the control circuit is configured to initiate a reduction in the voltage level of the storage capacitor to a minimum voltage level sufficient to operate the current measurement circuit and to provide the specified load current value.

8. The apparatus of claim 1, including:

a voltage reference circuit configured to provide a changeable reference voltage value; and a voltage converter circuit, communicatively coupled to the storage capacitor and the voltage reference circuit, configured to provide energy to the storage capacitor according to the reference voltage value, wherein the control circuit is configured to initiate adjustment of the voltage level of the storage capacitor by changing the reference voltage value.

9. The apparatus of claim 1, including:

a safety mechanism circuit communicatively coupled to the voltage measuring circuit and the control circuit, wherein the safety mechanism circuit is configured to monitor delivery of electrical energy during the constant current stimulation, and wherein the control circuit is configured to end the constant current stimulation when the safety mechanism circuit indicates that the electrical energy exceeds a specified energy level threshold.

10. A method comprising:

delivering quasi-constant current neural stimulation through a load from an electrostimulation energy storage capacitor using a medical device, including delivering quasi-constant current neural stimulation through the load in a first phase of energy delivery and delivering a voltage pulse to the load in a second phase of energy delivery;

obtaining, using the device, a measure of the quasi-constant current delivered to the load;

determining , according to the measure of quasi-constant current delivered to the load, a voltage level sufficient to source the measured quasi-constant current; and adjusting, using the device, the voltage level of the storage capacitor to the determined voltage level for a subsequent quasi-constant current neural stimulation.

11. The method of claim 10, including recurrently obtaining the measure of the delivered quasi-constant load current and adjusting the voltage level of the storage capacitor to minimize a difference between the measured quasi-constant current and the specified target load current.

12. The method of claim 10, including:

measuring a change in voltage of the storage capacitor from delivery of the quasi-constant current neural stimulation; and wherein obtaining a measure of current includes estimating the quasi-constant current delivered to the load from the measured change in voltage and duration of quasi-constant neural stimulation.

13. The method of claim 12, including delivering biphasic electrical neural therapy to the load, wherein delivering quasi-constant current neural stimulation includes delivering quasi-constant current neural stimulation during a first phase of the biphasic electrical neural therapy, and wherein measuring a change in voltage of the storage capacitor includes measuring the change during the first phase of the biphasic electrical neural therapy.

14. The method of claim 10, including measuring voltage across a sense resistor in series with the load, wherein obtaining a measure of current includes measuring the quasi-constant current delivered to the load using the measured voltage.

15. The method of claim 10, including:

obtaining a measure of resistance of the load, and wherein adjusting the voltage level of the storage capacitor includes adjusting the voltage level of the storage capacitor according to the determined resistance and the target load current.

16. The method of claim 10, wherein adjusting the voltage level of the storage capacitor includes reducing the voltage level of the storage capacitor to a minimum voltage level required to operate a current measuring circuit and to provide the specified target load current.

17. The method of claim 10, including:

charging a second capacitor using the constant current neural stimulation delivered through the load in the first phase; and wherein delivering a voltage pulse includes delivering a voltage pulse to the load from the second capacitor in the second phase of energy delivery.

18. The method of claim 10, including:

monitoring electrical energy delivered to the load during the quasi-constant current stimulation; and ending the quasi-constant current stimulation if at least one of the electrical energy exceeds a specified energy level threshold and a rate of discharge of the electrical energy exceeds a specified threshold discharge rate.

* * * * *